(12) United States Patent
Faham et al.

(10) Patent No.: US 6,723,348 B2
(45) Date of Patent: Apr. 20, 2004

(54) ORODISPERSIBLE TABLETS CONTAINING FEXOFENADINE

(75) Inventors: Amina Faham, Montréal (CA); Dominique Marechal, Laval (CA); Philippe Chenevier, Montréal (CA)

(73) Assignee: Ethypharm, Houdan (FR)

( * ) Notice: Subject to any disclaimer, the term of this patent is extended or adjusted under 35 U.S.C. 154(b) by 10 days.

(21) Appl. No.: 09/995,975

(22) Filed: Nov. 16, 2001

(65) Prior Publication Data

US 2003/0099700 A1 May 29, 2003

(51) Int. Cl.$^7$ ............... A61K 9/50; A61K 9/20
(52) U.S. Cl. ............ 424/490; 424/465; 424/458; 424/489; 424/495; 424/497
(58) Field of Search ............... 424/490, 465, 424/458, 489, 495, 497

(56) References Cited

U.S. PATENT DOCUMENTS

| | | | | |
|---|---|---|---|---|
| 4,254,129 A | * | 3/1981 | Carr et al. | 424/267 |
| 5,464,632 A | * | 11/1995 | Cousin et al. | 424/465 |
| 6,106,861 A | * | 8/2000 | Chauveau et al. | 424/465 |

FOREIGN PATENT DOCUMENTS

| | | |
|---|---|---|
| WO | WO 00/27357 | 5/2000 |
| WO | WO 00/51568 | 9/2000 |

OTHER PUBLICATIONS

H. Seager, "Drug–delivery Products and the Zydis Fast–dissolving Dosage Form" *J.Pharm. Parmacol. 1998*, 50:375–382.

* cited by examiner

*Primary Examiner*—Thurman K. Page
*Assistant Examiner*—Rachel M. Bennett
(74) *Attorney, Agent, or Firm*—Caesar, Rivise, Bernstein, Cohen & Pokotilow, Ltd.

(57) ABSTRACT

The present invention concerns orodispersible tablets, which are able to disintegrate in the buccal cavity upon contact with saliva by formation of an easy-to-swallow suspension, in less than 60 seconds, preferably in less than 40 seconds, containing fexofenadine in the form of coated granules, and a mixture of excipients comprising at least one disintegrating agent, a soluble diluent agent, a lubricant and optionally a swelling agent, a permeabilizing agent, sweeteners, flavoring agents and colors; the process for obtaining such orodispersible tablets and the coated granules incorporated therein and the use of said orodispersible tablets in the treatment of seasonal allergic rhinitis.

17 Claims, No Drawings

ORODISPERSIBLE TABLETS CONTAINING FEXOFENADINE

FIELD OF THE INVENTION

The present invention concerns orodispersible tablets comprising coated granules of fexofenadine. The invention also concerns said coated granules of fexofenadine, a process for the preparation thereof and the use of said orodispersible tablets.

In the context of the present invention, the term "orodispersible tablets" means tablets which are able to disintegrate in the buccal cavity in less than 60 seconds, preferably in less than 40 seconds, upon contact with saliva by formation of an easy-to-swallow suspension.

The disintegration time corresponds to the time between the moment when the tablet is placed in the buccal cavity in contact with saliva and the moment when the suspension (resulting from the disintegration without chewing of the tablet) is swallowed.

BACKGROUND OF THE INVENTION

Fexofenadine is a well known synthetic antiallergenic with the chemical name (±)-4-[1-hydroxy-4-[4 (hydroxydiphenylmethyl)-1-piperidinyl]-butyl]-$\alpha,\alpha$-dimethyl benzeneacetic acid.

Fexofenadine, a metabolite of terfenadine, is an antihistamine with selective peripheral H1-receptor antagonist activity.

Fexofenadine is known from e.g. U.S. Pat. No. 4,254,129. It is acknowledged in the art and is commercially available, in particular as an oral tablet or capsule, under the trade name Allegra®.

The tablets, commercially available under the trade name Allegra® contain 30, 60, or 180 mg fexofenadine hydrochloride (depending on the dosage) and, as excipients, croscarmellose sodium, magnesium stearate, microcrystalline cellulose and pregelatinized starch. Said tablets are coated with a film coating based on hydroxypropyl methylcellulose, mixture of iron oxides, polyethylene glycol, povidone, silicone dioxide, and titanium dioxide.

Fexofenadine is highly active via oral administration. While numerous pharmaceutical compositions for oral administration have been proposed, there still exists a need for commercially acceptable fexofenadine formulations for oral administration with good patient convenience and acceptance, especially for children or the elderly.

One particular difficulty in the formulation of fexofenadine in oral pharmaceutical compositions is its unpleasant, strong bitter taste and aftertaste.

Another difficulty in the formulation of fexofenadine in oral pharmaceutical compositions is the low solubility of fexofenadine, especially in gastric conditions (solubility of 0.2 mg of fexofenadine HCl per ml of pH 1.2 aqueous buffer solution).

It is therefore highly desirable to develop coated granules, containing fexofenadine, which have taste-masking properties while permitting rapid release of the active substance from the granules and allowing rapid absorption in the body after oral administration.

Furthermore, some patients, especially children and the elderly, experience difficulties swallowing the tablets, even with liquids.

It is estimated that 50% of the population have problems swallowing the tablets. This leads to poor, or even noncompliance, with the treatment and thus has a negative impact on the efficiency of the treatment (H. Seager, 1998, J. Pharm. Pharmacol 50, 375–382).

Oral disintegrable multiparticulate tablets have already been described in U.S. Pat. Nos. 5,464,632, 6,106,861, WO 00/27357 and WO00/51568, the contents of which are hereby incorporated by reference. The active ingredient is in the form of coated microcrystals or coated microgranules.

Up to now, no oral formulations of fexofenadine exist which are specifically suitable for patients having difficulties when swallowing or for patients taking the drugs with no liquids.

It is thus highly desirable to remedy this situation and to develop an orodispersible tablet, containing fexofenadine, which has taste-masking properties and presents a pleasant palatability such that the administration of the tablet is not unpleasant for the patient and which allows the obtaining of pharmacokinetic parameters at least bioequivalent to those which are obtained with conventional oral formulations of fexofenadine, for example tablets such as those available under the trademark Allegra®.

The Applicant has now surprisingly found that these characteristics can be obtained by formulating a tablet containing fexofenadine as active ingredient in the form of coated granules, and a mixture of excipients containing at least one disintegrating agent, a soluble diluent agent and a lubricant, and optionally a swelling agent, an antistatic agent, a permeabilising agent, sweeteners, flavoring agents and colors.

The present invention relates to orodispersible tablets which are able to disintegrate in the buccal cavity upon contact with saliva by formation of an easy-to-swallow suspension, in less than 60 seconds, preferably in less than 40 seconds, such tablets containing fexofenadine as active ingredient in the form of coated granules, and a mixture of excipients comprising at least one disintegrating agent, a soluble diluent agent, a lubricant and optionally a swelling agent, an antistatic agent, a permeabilising agent, sweeteners, flavoring agents and colors.

Surprisingly, although the tablets according to the invention disintegrate in the buccal cavity and present a release of the active ingredient which is equivalent to the conventional formulation, they nevertheless have a pleasant taste.

Furthermore, the orodispersible tablets of the invention are found to show high stability and physical integrity, e.g. during storage, handling, packaging and the like, while maintaining very good disintegration performance.

Fexofenadine may be used in the form of its racemate or a single enantiomer, in free base form or in acid addition salt form of the racemate or one of its single enantiomers. An acid addition salt form may be prepared from the free base form in a conventional manner and vice-versa. Examples of suitable acid addition salt forms include hydrochloride, lactate and ascorbate, preferably hydrochloride. Fexofenadine in the form of a hydrochloride salt is preferred.

In a preferred embodiment, fexofenadine particles present a particle size such that 100% of the particles have an average size of less than 20 $\mu$m.

In the tablets according to the invention, fexofenadine in anyone of said forms is present as coated granules.

In the present patent application, the term "fexofenadine" is employed for designating anyone of its specific forms.

According to an advantageous embodiment, the tablet according to the invention, has a hardness of not less than 15 N, when measured with the test method of the European Pharmacopeia (2.9.8).

According to an advantageous embodiment, the tablet according to the invention contains coated granules of fexofenadine, or one of its pharmaceutically acceptable salts, and a mixture of excipients, the ratio of the mixture of excipients to the coated granules is 0.4 to 9, preferably 1.5 to 5 and even more preferably 2 to 3 parts by weight, the mixture of excipients comprising:

- at least one disintegrating agent,
- a soluble diluent agent,
- a lubricant,
- and optionally a permeabilising agent, a swelling agent, an antistatic agent, sweeteners, flavoring agents and colors.

The disintegrating agent is selected from the group consisting of croscarmellose, available as e.g. Ac-di-sol®, crospovidone available as e.g. Kollidon CL®, and mixtures thereof.

According to an advantageous embodiment of the invention, the soluble diluent agent used in the tablets presents binding properties. The soluble diluent agent with binding properties consists of a polyol having less than 13 carbon atoms and being either in the form of a directly compressible product with an average particle size of 100 to 500 μm, or in the form of a powder with an average particle size of less than 100 μm, this polyol preferably being selected from the group comprising mannitol, xylitol, sorbitol and maltitol, it being understood that sorbitol cannot be used alone and that, in the case where there is only one soluble diluent agent with binding properties, it is used in the form of the directly compressible product, whereas in the case where there are at least two soluble diluent agents with binding properties, one is present in the directly compressible form and the other is present in powder form, it then being possible for the polyols to be the same, the ratio of directly compressible polyol to powder polyol being 99/1 to 20/80, preferably 80/20 to 20/80.

The proportion of disintegrating agent is from 3 to 15% by weight, preferably 5 to 15% by weight, in the case of a mixture, each disintegrating agent being comprised between 1 and 10% by weight, preferably 5 to 10% by weight, and the proportion of soluble diluent agent being 30 to 90% by weight, preferably 40 to 60% by weight, based in each case on the weight of the tablet.

The lubricant is selected from the group consisting of magnesium stearate, stearic acid, sodium stearyl fumarate, micronised polyoxyethyleneglycol (micronised Macrogol 6000), leukine, sodium benzoate and mixtures thereof.

The amount of lubricant is from 0 to 3%, preferably from 1 to 2% by weight, based on the weight of the tablet.

The lubricant can be dispersed within the mixture of excipients, or according to an advantageous embodiment, sprayed over the outer surface of the tablet. Thus, according to an advantageous embodiment of the tablets of the invention, the lubricant is in powder form and is, at least in part, disposed on the surface of the tablets.

The permeabilising agent allows the creation of a hydrophilic network which facilitates the penetration of saliva and hence assists the disintegration of the tablet.

The permeabilising agent is selected from the group comprising especially silica with a high affinity for aqueous solvents, such as colloidal silica (Aerosil®), precipitated silica (Syloïd® FP 244), maltodextrins, β-cyclodextrins and mixtures thereof.

The amount of permeabilising agent is between 0 and 5%, preferably from 0.5 to 2% by weight, based on the weight of the tablet.

A swelling agent can be incorporated in the mixture of excipients. Said swelling agent is selected from the group consisting of starch, modified starch or microcristalline cellulose.

An antistatic agent can be incorporated as a flow aid, said antistatic agent being selected from the group consisting of micronised or non micronised talc, fumed silica (Aerosil® R972), colloidal silica (Aerosil®200), precipitated silica (Syloïd® FP 244), and mixtures thereof.

The sweetener which can be included in the mixture of excipients, can be selected from the group consisting of especially aspartam, potassium acesulfame, sodium saccharinate, neohesperidin dihydrochalcone, sucralose, monoammonium glycyrrhizinate, and mixtures thereof.

The flavorings and colors are those conventionally used in pharmacy for the preparation of tablets.

The present invention also relates to the coated granules of fexofenadine or one of its pharmaceutically acceptable salts.

The taste-masking of fexofenadine is achieved by coating granulated microcrystals of fexofenadine with one or more polymers.

According to an advantageous embodiment of the invention, the granules of fexofenadine, or one of its pharmaceutically acceptable salts, are characterized in that the granules are coated and that they contain:

- microcrystals of fexofenadine, or one of its pharmaceutically acceptable salts,
- at least one binder,
- optionally a diluent agent, an antistatic agent, a sweetening agent and/or a coloring agent.

Furthermore, the granulation excipients can also include disintegrating agents and/or surfactants.

The binder is selected from the group consisting of cellulosic polymers, such as ethylcellulose, hydroxypropylcellulose and hydroxypropylmethyl cellulose, acrylic polymers, such as insoluble acrylate ammoniomethacrylate copolymer, polyacrylate or polymethacrylic copolymer, povidones, copovidones, polyvinylalcohols, alginic acid, sodium alginate, starch, pregelatinized starch, sucrose and its derivatives, guar gum, polyethylene glycol, preferably an acrylic polymer, most preferably Eudragit® E100, and mixtures thereof.

Optionally, in order to enhance the granulation of the fexofenadine or one of its pharmaceutically acceptable salts, a diluent agent is used.

The diluent agent is selected from the group consisting of microcrystalline cellulose, sucrose, dicalcium phosphate, starches, lactose and polyols of less than 13 carbon atoms, such as mannitol, xylitol, sorbitol, maltitol, pharmaceutically acceptable aminoacids, such as glycin, and their mixtures.

The antistatic agent, which can be used as flow aid, is selected from the group consisting of micronised or non micronised talc, fumed silica (Aerosil® R972), colloidal silica (Aerosil®200), precipitated silica (Syloïd® FP244) and mixtures thereof.

Conventional pharmaceutically acceptable sweetening agents and/or colouring agents can be incorporated into the granules of fexofenadine.

In a particular embodiment, the granule of fexofenadine or one of its pharmaceutically acceptable salts, is in the form of a core of granulated microcrystals of fexofenadine, coated with at least one layer comprising fexofenadine.

Said coated core is characterized in that the core and the layer comprise each from 70% to 95%, preferably 80% to 95% by weight of fexofenadine, or one of the pharmaceutically acceptable salts thereof, the balance to 100% being formed with at least one binder, and that said coated core is advantageously a sphere. Such a specific structure has previously been described by the Applicant in the French patent application FR 00 14803.

According to another embodiment of the invention, the granules comprise:
- from 10% to 95%, preferably from 50% to 70% of fexofenadine, or one of the pharmaceutically acceptable salts thereof,
- at most 20%, preferably at most 10% by weight of the binder, relative to the weight of fexofenadine, or one of the pharmaceutically acceptable salts thereof,
- at most 5%, preferably 2% by weight of the antistatic agent, relative to the weight of said granules
- optionally a diluent agent for the balance to 100%.

In order to ensure efficient taste masking, and a dissolution profile of the active substance such that more than 70% of the active substance is released in 30 minutes, preferably more than 90% is released in 30 minutes, the granules are coated with a coating composition containing at least one coating polymer selected from the group consisting of cellulosic polymers, acrylic polymers and their mixtures.

Among the cellulosic polymers, ethylcellulose, hydroxypropylcellulose (HPC) and hydroxypropylmethylcellulose (HPMC), are advantageously used.

Among the acrylic polymers, insoluble acrylate ammonio-methacrylate copolymer (Eudragit® RL100 or RS100 or Eudragit® RL30D or RS30D), polyacrylate (Eudragit®NE30D), or methacrylic copolymers (Eudragit® L100-55 or Eudragit® L30D, Eudragit® E100, Eudragit® EPO . . . ) are advantageously used, alone, in combination or in admixture with pH-dependent polymers. Eudragit® E100 or a mixture of Eudragit® EPO and Eudragit®NE30D are preferred.

In a preferred embodiment, the binder and the coating polymer are the same polymer.

The prepared coating liquid is either water-based or prepared with organic solvents. According to an advantageous embodiment, this coating liquid is suitable to be sprayed with conventional spray layering equipment, as for example a fluidized bed equipped with a top insert or bottom (würster) insert.

Optionally permeabilising agents, plasticizers, soluble agents, disintegrating agents and surfactants are added as coating additives.

The plasticizer is selected in the group consisting of triacetine, triethylacetate, triethylcitrate (Eudraflex®), ethylphthalate, or mixtures thereof. The plasticizer is used in proportions of at most about 30%, preferably 10% by weight of the coating polymers.

The soluble agents are selected in particular among the polyols having less than 13 carbon atoms.

The disintegrating agent or a surfactant which could be added during the granulation and the coating steps allow improved dissolution.

The surfactant may be an anionic, nonionic, cationic or amphoteric surfactant.

The disintegrating agent is selected from the group consisting of croscarmellose, available as e.g. Ac-di-sol®, crospovidone available as e.g. Kollidon CL®, and mixtures thereof.

The particle size range of coated granules comprising fexofenadine, or one of its pharmaceutically acceptable salts is adapted for obtaining an effective taste masking with an acceptable coating factor and a good mouthfeel.

Advantageously the coated granules according to the invention have a particle size distribution between 150 μm and 500 μm, preferably between 150 μm and 425 μm, such that at least 50%, preferably at least 70% of the granules have a particle size ranging between 150 and 425 μm and less than 15% of the granules have a particle size less than 150 μm. The particle sizes are measured according to conventional methods, preferably by sieving.

A granulation step is needed in order to obtain such particle size distribution.

In a particular embodiment, the coated granules according to the invention comprise:
- from 10% to 95%, preferably 40 to 75% of granules of fexofenadine, or one of its pharmaceutically acceptable salts, preferably fexofenadine HCl,
- from 5 to 90%, preferably 10 to 70% and even more preferably from 25 to 55% of a coating polymer, preferably Eudragit® E100, the percentages being expressed by weight relative to the weight of the granules of fexofenadine, or one of its pharmaceutically acceptable salts,
- from 0 to 10% of a permeabilising agent, preferably colloidal silica, the percentages being expressed by weight relative to the weight of the coating polymer.

Determination of workable proportions in any particular instance will generally be within the capability of the person skilled in the art. All indicated proportions and relative weight ranges described above are accordingly to be understood as being indicative of preferred or individually inventive teachings only and not as limiting the invention in its broadest aspect Details concerning any of the excipients of the invention may be found in Fiedler, H. P. "Lexikon der Hilfsstoffe für Pharmazie, Kosmetik und angrenzende Gebiete", Editio Cantor Verlag Aulendorf, Aulendorf, 4th revised and expanded edition (1996); "Handbook of Pharmaceutical Excipients", 2nd Edition, Editors A. Wade and P. J. Weller (1994), Joint publication of American Pharmaceutical Association, Washington, USA and The Pharmaceutical Press, London, England; or may be obtained from the relevant manufacturers, the contents of which are hereby incorporated by reference The invention also relates to a process for the preparation of coated granules of fexofenadine, which comprises the successive steps consisting in:
- dry mixing the microcrystals of fexofenadine or one of its pharmaceutically acceptable salts optionally with an antistatic agent and/or a diluent agent;
- granulating the mixture obtained in the above step by spraying of a solution or suspension of at least one binder,
- optionally applying a layer over the thus obtained granules by spraying thereon a suspension, or a solution comprising fexofenadine, or one of its pharmaceutically acceptable salts with at least one binder,
- coating the thus obtained granules with a suspension of a coating composition,
- drying the thus obtained coated granules.

The invention also concerns a process for preparing orodispersible tablets comprising coated granules of fexofenadine, or one of its pharmaceutically acceptable salts.

The process comprises the successive steps consisting in:
- dry mixing the microcrystals of fexofenadine, or one of its pharmaceutically acceptable salts, optionally with an antistatic agent, a diluent agent, a permeabilising agent, a sweetening agent and/or a coloring agent;
- granulating the thus obtained mixture by spraying thereon a solution or a suspension of at least one binder,
- optionally applying a layer over the thus obtained granules by spraying thereon a suspension, or a solution comprising fexofenadine, or one of its pharmaceutically acceptable salts with at least one binder.

coating the thus obtained granules by spraying thereon a suspension, a dispersion or a solution of the coating composition, drying the thus obtained coated granules, dry mixing coated granules and a mixture of excipients consisting of at least one disintegrating agent, a soluble diluent agent, and optionally a lubricant, a permeabilising agent, a swelling agent, sweeteners, an antistatic agent, flavorings and colors, compressing the mixture of coated granules and excipients into a tablet.

The lubricant can be mixed with the excipients for the tablet, but can advantageously be sprayed on the surface of the punches before tabletting.

In this process the mixing, granulating and coating steps can be performed in different or in the same equipment, each step being performed in the presence of a mixture of excipients which are identical or different.

For granulating, high shear mixer, planetary mixer or fluidized bed with insert used for bottom spray, granulation, tangential spray granulation, top spray granulation can be used, bottom spray granulation being preferred.

In an advantageous embodiment, each step is performed on a fluidized air-bed, such as for example, but not limited to Glatt GPCG-1, GPCG-3, GPCG-5 or GPCG 120.

For coating, bottom, top and tangential spray methods can be used as well as layering method, bottom spray method of coating being preferred.

For compressing the mixture of coated granules and excipients into a tablet, various punches may be used, with diameters comprised between 8 and 17 mm, depending upon the dosage of the tablet.

Various shapes may be used, such as for example, flat shape, advantageously with bevelled edges or polo punches.

The orodispersible tablets of the present invention show rapid disintegration in the buccal cavity upon contact with saliva without chewing, in less than 60 seconds, preferably in less than 40 seconds, have a pleasant taste and palatability and thus have particularly good patient convenience and patient acceptance due to their increased ease of administration and ingestion.

In addition the tablets of the invention show surprisingly high physical stability and are easy to handle and package.

According to a preferred embodiment, the tablet of the invention presents the following composition:

granules of Fexofenadine HCl coated with Eudragit® E100, and a mixture of excipients consisting of Eudragit® E100, mannitol powder, mannitol granular, Crospovidone, precipitated silica, sweeteners and flavors.

For the preparation of said tablets, isopropanol is used as solvent and removed during the coating and granulation processes.

According to an advantageous embodiment, the tablet of the invention has the following composition:

| Fexofenadine coated granules | |
|---|---|
| Fexofenadine HCl | 40–80% |
| Eudragit ® E100 | 20–60% |
| Precipitated silica | 0–5% | the percentages being calculated by weight of coated granules,

| Excipients for the formulation of the tablet | |
|---|---|
| Fexofenadine coated granules | 10–45% |
| Mannitol powder and/or granular | 50–90% |
| Crospovidone | 2–15% |
| Precipitated silica | 0–5% |
| Magnesium stearate | 0–5% |
| Sucralose | 0–5% |
| Flavors | 0–2% | the percentages being calculated by weight of the tablet.

For the preparation of said tablets, isopropanol is used as solvent and removed during the coating and granulation processes.

The tablets are particularly effective in treating seasonal allergic rhinitis, in adults and children 6 years of age and older.

The present invention also concerns the use of a coated granules of fexofenadine with a mixture of excipients, as described above, for the manufacture of a medicament for the treatment of symptoms associated with seasonal allergic rhinitis.

The present invention relates also to methods for the treatment of symptoms associated with seasonal allergic rhinitis, in which the tablets of fexofenadine according to the invention are orally administered.

Symptoms treated effectively include sneezing, rhinorrhea, itchy nose/palate/throat, itchy/watery, rhinitis.

The utility of the tablets of the present invention may be observed in standard bioavailability tests or standard animal models, for example ascertaining dosages of the present tablets giving blood levels of fexofenadine hydrochloride equivalent to blood levels having a therapeutical effect on administration of known fexofenadine oral dosage forms, e.g. a tablet.

The appropriate dosage will, of course, vary depending upon, for example, the host and the nature and severity of the condition being treated. However, in general satisfactory results in animals are indicated to be obtained by daily treatments. In humans an indicated daily dosage is in the range from about 10 mg to about 500 mg per day, preferably from 30 mg to 180 mg, conveniently administered, for example, in divided doses up to four times a day or once daily. Preferred dosages, expressed as fexofenadine HCl, for children 6 to 11 years of age are about 30 mg two times a day, and for adults and children 12 years of age and older from about 60 mg two times a day, or 180 mg once a day.

The invention is illustrated more in detail in the following examples.

EXAMPLES

Particle size of Fexofenadine HCl used for the manufacture of granules of examples 1 to 4 is measured with conventional laser equipment.

Particle size distribution has following characteristics:

| | |
|---|---|
| $D_{10\%}$ | 2.1 µm |
| $D_{50\%}$ | 5.3 µm |
| $D_{90\%}$ | 11.1 µm |

In the examples below, the following excipients are used:

Methacrylic polymer sold under tradename Eudragit®EPO or Eudragit® E100.

Polyacrylate sold under the tradename Eudragit® NE30D.

Mannitol powder
Mannitol granular 300
Sucralose
Aspartam
Peppermint, wildberry as flavoring agents
Precipitated silica sold under the name Syloïd FP244
Polyvinylpyrrolidone sold under the name PVP K90.

Examples 1 to 4 relate to the preparation of coated granules of fexofenadine.

Example 1

Granulating Step 500 g of fexofenadine HCl mixed with 15 g of Syloïd FP 244 were granulated in a fluidized bed with 465 g of a mixture of Eudragit EPO/Eudragit NE30D (50/50) in water at 16% (weight/weight).

Coating Step

The thus obtained granules were coated in a fluidized bed equipped with a top insert, by spraying thereon a dispersion of 465 g of a mixture of Eudragit EPO/Eudragit NE30D (50/50) in water at 16% (weight/weight).

The amount of coating was of 12.5% by weight with respect to the weight of the granules of fexofenadine HCl.

The dissolution rates of the thus obtained coated granules were measured with the following method:

Apparatus: USP Apparatus II (Paddle method)
Speed: 50 rpm
Volume: 900 mL of HCl 0.001N pH 3.0*
Temperature: 37.0° C.±0.5° C.
Sampling (5 mL): 2.5, 7.5, 15, 30 and 60 minutes
HPLC Detection: UV at 220 nm
HPLC column: Zorbax SB-Phenyl, 5 µm, 4.6×250 mm.
Injection volume: 20 µL
Mobile Phase: Acetonitrile: 0.03 M Acetic acid containing Triethylamine pH 5.25 (36:64).
Dissolution medium: HCl 0.001N adjusted to pH 3.0±0.05 (if necessary) with o-Phosphoric acid.

The results are given in the following table 1:

TABLE 1

| | Dissolved fexofenadine in % (w/w) |
|---|---|
| 5 minutes | 55% |
| 10 minutes | 70% |
| 15 minutes | 75% |
| 30 minutes | 85% |

More than 80% of fexofenadine is dissolved after 30 minutes, taste-masking is efficient.

Example 2

Granulating Step 500 g of fexofenadine HCl mixed with 15 g of Syloïd FP244 were granulated in a fluidized bed with 30 g of an aqueous solution of PVP K90 at 8% (weight/weight).

Coating Step

The thus obtained granules were coated in a fluidized bed equipped with a top insert, by spraying thereon a mixture of Eudragit EPO/Eudragit NE30D (60/40) in water at 16% (weight/weight)

The amount of coating was of 40% by weight with respect to the weight of the granules of fexofenadine HCl.

The particle size distribution (Sieve method) is given in the following table.

TABLE 2

| Sieve operture | After Granulating step | After Coating step |
|---|---|---|
| >0.500 mm | 14.5% | 5.7% |
| 0.425 mm–0.500 mm | 13.0% | 24.1% |
| 0.355 mm–0.425 mm | 20.0% | 9.5% |
| 0.250 mm–0.355 mm | 30.5% | 28.9% |
| 0.150 mm–0.250 mm | 21.5% | 31.5% |
| <0.150 mm | 0.5% | 0.3% |

The dissolution rates of said granules were measured as indicated in example 1 above.

The results are given in the following table 3:

TABLE 3

| | Dissolved fexofenadine in % (w/w) |
|---|---|
| 5 minutes | 65% |
| 10 minutes | 85% |
| 15 minutes | 100% |
| 30 minutes | 100% |

More than 80% of fexofenadine is dissolved after 30 minutes, taste-masking is efficient.

Example 3

Granulating Step 1000 g of fexofenadine HCl mixed with 30 g of Syloïd FP 244 were granulated in a fluidized bed equipped with a Wurster insert with 1500 g of an solution of Eudragit E100 in isopropanol at 12% (weight/weight).

Coating Step

The thus obtained granules were coated in a fluidized bed equipped with a top insert, by spraying thereon a polymeric dispersion of 3900 g of Eudragit E100 in isopropanol at 12% (weight/weight) containing 1% of Syloïd FP 244.

The amount of coating was of 38% by weight with respect to the weight of the granules of fexofenadine HCl.

The particle size distribution (Sieve method) is given in the following table.

TABLE 4

| Sieve operture | Coated granules |
|---|---|
| >0.600 mm | 0% |
| 0.500 mm–0.600 mm | 1.0% |
| 0.425 mm–0.500 mm | 9.2% |
| 0.355 mm–0.425 mm | 18.6% |
| 0.250 mm–0.355 mm | 36.2% |
| 0.150 mm–0.250 mm | 30.2% |
| 0.090 mm–0.150 mm | 3.4% |
| <0.090 mm | 1.4% |

The dissolution rates of said granules were measured as indicated in example 1 above.

The results are given in the following table 5:

TABLE 5

| | Dissolved fexofenadine in % (w/w) |
|---|---|
| 5 minutes | 55% |
| 10 minutes | 85% |
| 15 minutes | 95% |
| 30 minutes | 100% |

More than 80% of fexofenadine is dissolved after 30 minutes, taste-masking is efficient.

Example 4

Granulating Step

1000 g of fexofenadine HCl mixed with 30 g of Syloïd FP 244 were granulated in a planetary mixer with 400 g of an solution of Eudragit E100 in isopropanol at 12% (weight/weight)

Coating Step

The obtained granules were coated in a fluidized bed equipped with a Wurster insert, by spraying thereon a solution of Eudragit E100 in isopropanol at 10% (weight/weight) containing 1% of Syloïd FP 244.

The amount of coating was of 30% by weight with respect to the weight of the granules of fexofenadine HCl.

The dissolution rates of said granules were measured as indicated in example 1 above.

The results are given in the following table 6:

TABLE 6

|  | Dissolved fexofenadine in % (w/w) |
| --- | --- |
| 5 minutes | 40% |
| 10 minutes | 80% |
| 15 minutes | 95% |
| 30 minutes | 100% |

100% of fexofenadine is dissolved after 30 minutes, taste-masking is efficient.

Examples 5–8 relate to the preparation of tablets.

Example 5

Three types of tablets T1, T2, T3 were prepared using coated granules of fexofenadine presenting different coating ratios. The coated granules of fexofenadine were obtained as in example 3 above but using the three different coating ratios of 30, 35 and 40. Then, an amount of each type of said coated granules corresponding to 180 mg of fexofenadine HCl was thoroughly blended for 15 minutes with the following tablet excipients.

| Crospovidone | 10% |
| --- | --- |
| Silica | 0.5% |
| Magnesium stearate | 0.5% |
| Aspartame | 2% |
| Flavor | 1%. |
| Mannitol powder (60 μm)/granular (330 μm) (2/1) | qs 100% |

The percentages are expressed as percentage of the total weight of a tablet.

The homogeneous obtained blend was introduced in a tabletting machine equipped with 14 mm-diameter polo shape punches.

These tablets T1, T2 and T3 were obtained.

For each tablet thus obtained, the weight, hardness, disintegrating time in mouth, mouthfeel and taste were measured.

The results are displayed in the table 7

TABLE 7

| Tablets | T1 | T2 | T3 |
| --- | --- | --- | --- |
| Coated granule ratio (% by weight) | 30 | 35 | 40 |
| Weight | 920 mg | 780 mg | 690 mg |
| Hardness | 44 N | 39 N | 45 N |
| Disintegration time in mouth | 15–20 sec. | 15–20 sec. | 20–25 sec. |
| Mouthfeel | Complies | Complies | Complies |
| Taste | Complies | Complies | Complies |

T1, T2, T3 present an acceptable dissolution rate with good taste and pleasant mouthfeel and disintegrate in buccal cavity in less than 30 seconds.

Example 6

As in example 5, three types of tablets (T4, T5, T6) presenting coated granules of fexofenadine with coating ratios of 30, 35, 40 were prepared but using an amount of fexofenadine HCl equivalent to 30 mg per tablet.

The homogeneous obtained blend was introduced in a tabletting machine equipped with polo shape punches as described in the table.

Results are displayed in the table 8

TABLE 8

| Tablets | T4 | T5 | T6 |
| --- | --- | --- | --- |
| Coated granule ratio (% by weight) | 30 | 35 | 40 |
| Punch diameter | 8 mm | 7 mm | 6 mm |
| Weight | 153 mg | 131 mg | 115 mg |
| Hardness | 44 N | 39 N | 45 N |
| Disintegration time in mouth | 15–20 sec. | 15–20 sec. | 20–25 sec. |
| Mouthfeel | Complies | Complies | Complies |
| Taste | Complies | Complies | Complies |

Tablets T4, T5 and T6 present an acceptable taste and pleasant mouthfeel and disintegrate in buccal cavity in less than 30 seconds.

Example 7

Tablets T7 according to the formula of T2 of example 5 are manufactured, using a ratio of Mannitol powder/Mannitol granular ratio of 1/1, containing an amount of fexofenadine HCl equivalent to 180 mg per tablet.

The homogeneous obtained blend was introduced in a tabletting machine equipped with 14 mm-diameter polo shape punches.

The disintegration time in the mouth, the mouthfeel and taste were evaluated.

The results are displayed in the table 9.

TABLE 9

| Tablets | T7 |
| --- | --- |
| Disintegration time in mouth | 25 sec. |
| Mouthfeel | Complies |
| Taste | Complies |

Tablets T7 with a mannitol powder/granular ratio of 1/1 (w/w) present a good taste and pleasant mouthfeel and disintegrate in buccal cavity in less than 30 seconds.

Example 8

Three types of tablets (T8, T9, T10) according to the formula T2 of example 5 were manufactured but using three different ratios of crospovidone of 5, 7.5 and 10% by weight.

The homogeneous obtained blend was introduced in a tabletting machine equipped with 14 mm-diameter polo shape.

Tablets T8, T9 and T10 were thus obtained. The disintegrating time in mouth, the hardness, the mouthfeell and taste were evaluated, the results are displayed in table 10.

TABLE 10

| Tablets | T8 | T9 | T10 |
|---|---|---|---|
| Crospovidone ratio (% by weight) | 5 | 7.5 | 10 |
| Hardness | 44 N | 45 N | 45 N |
| Disintegration time in mouth | 20–25 sec. | 20–25 sec. | 20–25 sec. |
| Mouthfeel | Complies | Complies | Complies |
| Taste | Complies | Complies | Complies |

Tablets T8, T9 and T10 present an acceptable taste and pleasant mouthfeel and disintegrate in buccal cavity in less than 30 seconds.

Exemple 9

Pharmacokinetic Studies

A bioequivalence study was conducted with two tablets (T11 and T12) according to the invention versus Allegra® 180 mg (Reference).

15 subjects received T11 versus Reference and 13 subjects received T12, each versus Reference The respective compositions of T11 and T12 are given below:

|  | T11 | T12 |
|---|---|---|
| Fexofenadine HCl coated granules | | |
| Fexofenadine HCl | 48.4% | 58.2% |
| Eudragit E100 | 47.4% | 37.7% |
| Silica | 4.2% | 4.1% |
| Tablets | | |
| Coated granules corresponding to 180 mg of Fexofenadine HCl | | 30% |
| Crospovidone | | 5% |
| Silica | | 0.5% |
| Magnesium stearate | | 1% |
| Sucralose | | 2% |
| Flavor | | 0.2% |
| Mannitol powder (60 µm)/ granular (330 µm) (1/1) | | qs 100% |

Said tablets were prepared according to the process of example 5 above. The tablets (Prototype and Reference) were administered to fasting patients. Pharmacokinetic parameters obtained for each prototype A and B and Reference are listed in tables 11 and 12:

TABLE 11

| Test 1 (n = 15) – mean values | AUC (CV) | Cmax (CV) | Tmax (CV) |
|---|---|---|---|
| Reference | 3132,2 | 453,8 | 2,0 |
| T11 | 3804,4 | 571,2 | 2,9 |
| (% as exp. versus reference) | (121) | (126) | (144) |

T11 under fasting conditions has slightly higher bioavailability relative to the reference.

TABLE 12

| Test 2 (n = 13) – mean values | AUC | Cmax | Tmax |
|---|---|---|---|
| Reference | 3017,0 | 457,3 | 2,2 |
| T12 | 3047,1 | 409,8 | 2,6 |
| (% as exp. versus reference) | (101) | (90) | (115) |

T12 under fasting is bioequivalent relative to the reference tablet.

What is claimed is:

1. Orodispersible tablets, which are able to disintegrate in the buccal cavity upon contact with saliva by formation of an easy-to-swallow suspension, in less than 60 seconds containing:
    (i) fexofenadine selected from the group consisting of fexofenadine base and at least one of its pharmaceutically acceptable salts, the form of coated granules, and
    (ii) a mixture of excipients comprising at least one disintegrating agent, soluble diluent agent, and a lubricant.

2. Orodispersible tablets according to claim 1, which are able to disintegrate in less than 40 seconds.

3. Orodispersible tablets according to claim 1, wherein the mixture of excipients further comprises a swelling agent, an antistatic agent, a permeabilising agent, sweeteners, flavoring agents or colors.

4. Orodispersible tablets according to claim 1, wherein the weight ratio of the mixture of excipients to the coated granules is 0.4 to 9.

5. Orodispersible tablets according to claim 4, wherein the weight ratio of the mixture of excipients to the coated granules is 1.5 to 5.

6. Orodispersible tablets according to claim 5, wherein the weight ratio of the mixture of excipients to the coated granules is 2 to 3.

7. Orodispersible tablets according to claim 1, wherein disintegrating agent is selected from the group consisting of croscarmellose, crospovidone, and mixtures thereof.

8. Orodispersible tablets according to claim 1, wherein the soluble diluent agent has binding properties and consists of a polyol having less 13 carbon atoms and being either in the form of the directly compressible product with an average particle size of 100 to 500 µm, or in the form of a powder with an average particle size of less than 100 µm, it being understood that sorbitol cannot be used alone and that, in the case where there is only one soluble diluent agent with binding properties, it is used in the form of the directly compressible product, whereas in the case where there are at least two soluble diluent agents with binding properties, one is present in the directly compressible form and the other is present in powder form, it then being possible for the polyols to be the same, the ratio of directly compressible polyol to powder polyol being 99/1 to 20/80.

9. Orodispersible tablets according to claim 1, wherein the proportion of disintegrating agent is from 3 to 15% by weight, and the proportion of soluble diluent agent is 30 to 90% by weight, the percentages being based on the weight of the tablet.

10. Orodispersible tablets according to claim 9, wherein the proportion of disintegrating agent is from 5 to 15% by weight, and the proportion of soluble diluent agent is from 40 to 60% by weight, the percentages being based on the weight of the tablet.

11. Orodispersible tablets according to claim 1, wherein the lubricant is selected from the group consisting of magnesium stearate, stearic acid, sodium stearyl fumarate, micronised polyoxyethyleneglycol, leukine, sodium benzoate and mixtures thereof.

12. Orodispersible tablets according to claim 3, wherein the sweetener is selected from the group consisting of aspartam, potassium acesulfame, sodium saccharinate, neohesperidin dihydrochalcone, sucralose, monoammonium glycyrrhizinate, and mixtures thereof.

13. Orodispersible tablets according to claim 11, wherein the lubricant is in powder form and is, at least in part, disposed on the surface of the tablets.

14. Method of treatment of symptoms associated with seasonal allergic rhinitis wherein orodispersible tablets according to claim 1 is orally administered to patients.

15. Orodispersible tablet of fexofenadine or one of its pharmaceutically acceptable salts, according to claim 1, which is bioequivalent to Allegra® tablet in a bioavailability study in humans.

16. Orodispersible tablets according to claim 8, wherin the polyol is selected from the group consisting of mannitol, xylitol, sorbitol and maltitol.

17. Orodispersible tablets according to claim 8, wherin the ratio of directly compressible polyol to powder polyol is 80/20 to 20/80.

* * * * *

UNITED STATES PATENT AND TRADEMARK OFFICE
CERTIFICATE OF CORRECTION

PATENT NO. : 6,723,348 B2
DATED : April 20, 2004
INVENTOR(S) : Amina Faham, Dominique Marechal and Philippe Chenevier It is certified that error appears in the above-identified patent and that said Letters Patent is hereby corrected as shown below:

Column 14,
Line 17, insert -- in -- before "the form of coated granules"
Line 19, insert -- a -- between "integrating agent," and "soluble diluent agent"

Column 16,
Lines 5 and 8, "wherin" should read -- wherein --

Signed and Sealed this

Seventeenth Day of August, 2004

JON W. DUDAS
*Acting Director of the United States Patent and Trademark Office*